US005556895A

United States Patent [19]

Lipinsky et al.

[11] Patent Number: 5,556,895
[45] Date of Patent: Sep. 17, 1996

[54] DEGRADABLE POLYDIOXANEONE-BASED MATERIALS

[75] Inventors: Edward S. Lipinsky, Worthington; Richard G. Sinclair; James D. Browning, both of Columbus, all of Ohio; Alex Cheung, Ft. Collins, Colo.; Kevin H. Schilling, Arvada, Colo.; Dan W. Verser, Golden, Colo.

[73] Assignee: Ecopol LLC, Golden, Colo.

[21] Appl. No.: 455,990

[22] Filed: May 31, 1995

Related U.S. Application Data

[63] Continuation of Ser. No. 127,907, Sep. 29, 1993, which is a continuation-in-part of Ser. No. 854,559, Mar. 19, 1992, Pat. No. 5,319,107, and Ser. No. 949,675, Sep. 22, 1992, abandoned, which is a continuation-in-part of Ser. No. 579,000, Sep. 6, 1990, Pat. No. 5,216,050, Ser. No. 579,005, Sep. 6, 1990, Pat. No. 5,180,765, Ser. No. 579,460, Sep. 6, 1990, Pat. No. 5,252,642, and Ser. No. 579,465, Sep. 6, 1990, abandoned, said Ser. No. 579,000, Ser. No. 579,005, Ser. No. 579,460, and Ser. No. 579,465, each is a continuation-in-part of Ser. No.387,676, Jul. 31, 1989, abandoned, Ser. No. 387,678, Jul. 31, 1989, abandoned, Ser. No. 386,844, Jul. 31, 1989, abandoned, and Ser. No. 387,670, Jul. 31, 1989, abandoned, said Ser. No. 387,676, Ser. No. 387,678, Ser. No. 386,844, and Ser. No. 387,670, each is a continuation-in-part of Ser. No.229,894, Aug. 8, 1988, abandoned, Ser. No. 229,896, Aug. 8, 1988, abandoned, Ser. No. 317,391, Mar. 1, 1989, abandoned, and Ser. No. 229,939, Aug. 8, 1988, abandoned, said Ser. No. 854,559, is a continuation-in-part of Ser. No. 584,126, Sep. 18, 1990, Pat. No. 5,274,127.

[51] Int. Cl.$^6$ ..................................................... C08J 9/00
[52] U.S. Cl. ............................................. 521/182; 521/916
[58] Field of Search ................................. 521/182, 916

[56] References Cited

U.S. PATENT DOCUMENTS

| | | | |
|---|---|---|---|
| 2,703,316 | 3/1955 | Schneider | 260/78.3 |
| 2,768,973 | 10/1956 | Castle et al. | 260/602 |
| 3,636,956 | 1/1972 | Schneider. | |
| 3,773,737 | 11/1973 | Goodman et al. | 250/78 A |
| 3,797,499 | 3/1974 | Schneider | 128/334 R |
| 3,867,190 | 2/1975 | Schmitt et al. | 117/138.8 A |
| 3,960,152 | 6/1976 | Augurt et al. | 128/335.5 |
| 4,440,789 | 4/1984 | Mattei et al. | 424/78 |
| 4,766,182 | 8/1988 | Murdock et al. | 521/182 |
| 4,797,468 | 1/1989 | De Vries | 528/354 |
| 4,800,219 | 1/1989 | Murdoch et al. | 525/413 |
| 4,835,293 | 5/1989 | Bhatia | 549/274 |
| 4,891,263 | 1/1990 | Kotlair et al. | 428/225 |
| 4,990,222 | 2/1991 | Aigner et al. | 203/91 |
| 5,028,667 | 7/1991 | McLain et al. | 525/415 |
| 5,053,485 | 10/1991 | Nieuwenhuis et al. | 528/354 |
| 5,053,522 | 10/1991 | Muller | 549/274 |
| 5,076,807 | 12/1991 | Bezwada et al. | 606/230 |
| 5,076,983 | 12/1991 | Loomis et al. | 264/101 |
| 5,084,051 | 1/1992 | Törmälä et al. | 606/77 |
| 5,089,632 | 2/1992 | Paul | 549/274 |
| 5,120,802 | 6/1992 | Mares et al. | 525/415 |
| 5,134,171 | 7/1992 | Hommel et al. | 521/182 |
| 5,138,074 | 8/1992 | Bellis et al. | 549/274 |
| 5,196,551 | 3/1993 | Bhatia et al. | 549/274 |
| 5,235,031 | 8/1993 | Drysdale et al. | 528/354 |
| 5,236,560 | 8/1993 | Drysdale et al. | 203/99 |
| 5,238,968 | 8/1993 | Morita et al. | 521/182 |
| 5,254,718 | 10/1993 | Anton et al. | 560/55 |
| 5,274,127 | 12/1993 | Sinclair et al. | 549/274 |
| 5,319,107 | 6/1994 | Benecke et al. | 549/274 |
| 5,332,839 | 7/1994 | Benecke et al. | 549/274 |
| 5,359,027 | 10/1994 | Perego et al. | 528/354 |
| 5,447,962 | 9/1995 | Ajoka et al. | 521/182 |

FOREIGN PATENT DOCUMENTS

| | | |
|---|---|---|
| 0261572 | 3/1988 | European Pat. Off. . |
| 1122229 | 7/1968 | United Kingdom . |
| WO91/17155 | 11/1991 | WIPO . |
| WO93/04112 | 3/1993 | WIPO . |

OTHER PUBLICATIONS

Alen et al., "Condensation of Glycolic, Lactic and 2-Hydroxybutanoic Acids during Heating and Identification of the Condensation Products by GLC–MS", pp. 633–636, 1980, *Acta Chem. Scand.*, B34, No. 9.

Bezzi, "Transformation of Cyclic Esters into Linear Polyesters", pp. 215–224, 1938, *Gazz. Chim. Ital.*, 68.

Deibig, et al., "Polytetramethyl Glycolide II. Thermal Behavior of Polytetramethyl Glycolide", pp. 133–139, 171, 1989, *Die Makromolekulare Chemie*, 145 (Nr. 3631).

Deibig, et al. "Polytetramethyl Glycolide I. Synthesis and Properties of Polytetramethyl Glycolide", pp. 123–131, 1971, *Die Makromolekulare Chemie*, 145 (Nr. 3630).

Fukuzaki et al., "Low–Molecular–Weight Copolymers Compsed of L–lactice Acid and Various DL–hydroxy Acids as Biodegradable Carriers", pp. 2571–2577, 1989, *Makromol. Chem.*, 190.

Fukuzaki et al., "Synthesis of Biodegradable Poly(L–lactic Acid–co–D,L,–mandelic Acid) with Relatively Low Molecular Weight", pp. 2407–2415, 1989, *Makromol. Chem.*, 190.

*Primary Examiner*—Morton Foelak
*Attorney, Agent, or Firm*—Sheridan Ross & McIntosh

[57] ABSTRACT

Disclosed are degradable materials including molded products, laminates, foams, nonwoven materials, adhesives, coatings and films, and particularly packaging films. The materials are made using polydioxaneone polymers comprising at least two different dioxaneone-based repeating units. Preferred polymers are polydioxanediones. First repeating units have less carbon atoms in constituent groups extending from the polymer backbone than second repeating units. Physical characteristics and degradation of the materials can be varied by varying the choice and/or relative proportions of first and second repeating units in the poldioxaneone polymers. Methods for preparing polydioxaneone polymers that can be used in the manufacture of the materials are also discussed, as are suitable monomers and methods for preparing such monomers.

15 Claims, No Drawings

DEGRADABLE POLYDIOXANEONE-BASED MATERIALS

CROSS-REFERENCE TO RELATED APPLICATIONS

This application is a continuation of U.S. application Ser. No. 08/127,907 by Lipinsky et al., filed Sep. 29, 1993, which is a continuation-in-part of U.S. application Ser. No. 07/854 559 for "Method to Produce Cyclic Esters" by Benecke et al. filed Mar. 19, 1992, now U.S. Pat. No. 5,319,107, which is a continuation-in-part of U.S. application Ser. No. 07/584, 126 for "Lactide Production from Dehydration of Aqueous Lactic Acid Feed" by Sinclair et al., now U.S. Pat. No. 5,274,127 which was filed Sep. 18, 1990 and which is incorporated herein by reference in its entirety. application Ser. No. 127,907 is also a continuation-in-part of U.S. patent application Ser. No. 07/949,675 for "Degradation Control of Degradable Polymers" by Sinclair et al., filed Sep. 22, 1992, now abandoned which is a continuation-in-part of U.S. patent application Ser. Nos. 07/579,000 for "Blends of Polylactic Acid" by Sinclair, now U.S. Pat. No. 5,216,050 issued Jun. 1, 1993; 07/579,005 for "Biodegradable Thermoplastic from Polylactic Acid" by Sinclair, now U.S. Pat. No. 5,180,765 issued Jan. 19, 1993; 07/579,460 for "Degradable Impact Modified Polylactic Acid" by Sinclair, now U.S. Pat. No. 5,252,642; and 07/579,465 for "Biodegradable Replacement for Crystal Polystyrene" by Sinclair et al., now abandoned all of which were filed on Sep. 6, 1990 and which are, respectively, continuation-in-parts of U.S. application Ser. Nos. 07/387,676; 07/387,678; 07/386,844; and 07/387,670 all of which were filed on Jul. 31, 1989, all of which are now abandoned and which are, respectively, continuation-in-parts of U.S. patent application Ser. Nos. 07/229,894, filed Aug. 8, 1988; 07/229,896 filed Aug. 8, 1988; 07/317,391 filed Mar. 1, 1989; and 07/229,939 filed Aug. 8, 1988, all now abandoned; all of which are incorporated by reference herein in their entirety.

FIELD OF THE INVENTION

The present invention relates to degradable materials made from polydioxaneones and monomers and methods for making the same. Degradable materials include molded products, laminates, foams, nonwoven materials, adhesives, coatings and films, and particularly packaging films.

BACKGROUND OF THE INVENTION

Some polymers are known to degrade by hydrolysis in the presence of water and thereby decompose to smaller chemical units. Some of these polymers are also biodegradable, such as polylactide, polyglycolide, poly-ε-caprolactone and polydioxaneone (2-keto-1,4-dioxane).

Polymers such as polylactide, polyglycolide, and poly(2-keto-1,4-dioxane) can be referred to generally as polydioxanediones, because each is prepared by polymerization of a dioxanedione-based monomer. As used herein, except as specifically noted otherwise, dioxaneone refers to compounds having a dioxane ring with at least one carbonyl oxygen pendant from the dioxane ring. The remaining three carbon atoms in the dioxane ring may have various constituents pendant therefrom. Although the term dioxaneone, which is also sometimes written as dioxanone, is often used in a specific sense to refer to 2-keto-1,4-dioxane, dioxaneone is used herein in a general sense as discussed below, unless otherwise specifically indicated by the general formula:

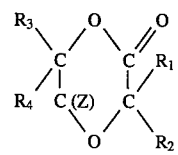

where $R_1$, $R_2$, $R_3$ and $R_4$ can be any of a variety of constituents and where Z can be one or more constituents covalently bonded to the associated tetravalent carbon atom in the dioxane ring. When all of $R_1$, $R_2$, $R_3$ and $R_4$ are hydrogen and Z is two hydrogen constituents, then the compound is 2-keto-1,4-dioxane.

Dioxaneones such as lactide and glycolide, in which Z is a carbonyl oxygen, may be more specifically referred to as dioxanediones since they each have two carbonyl oxygens pendant from the dioxane ring. Dioxanediones are cyclic diesters that may be represented by the general formula:

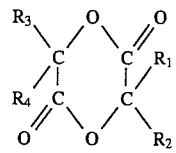

Where $R_1$, $R_2$, $R_3$ and $R_4$ can be any of a variety of constituents. When $R_1$, $R_2$, $R_3$, and $R_4$ are all hydrogen, then the compound is glycolide which is also referred to as 1,4-dioxane-2,5-dione. Although the term dioxanedion is sometimes used to refer specifically to glycolide, the term as used herein is always employed in the general sense to indicate a class of compounds as indicated by the generic formula above, except as otherwise noted herein. When $R_1$ and $R_3$ are methyl and $R_2$ and $R_4$ are hydrogen the compound is lactide, which may be also referred to as 3,6-dimethyl-1,4-dioxane- 2,5-dione. A polydioxaneone having one or more repeating units representative of a dioxanedione monomer may be more specifically referred to as a polydioxanedione. When a dioxaneone contains one or more asymmetrical carbon atoms, such as is the case with lactide, then that particular dioxaneone can exist as various optical isomers. For example, lactide can exist as two optically active isomers, D-lactide and L-lactide, or as the optically inactive isomer meso-lactide. D-lactide and L-lactide can also be present in equal quantities to form an optically inactive mixture known as racemic-lactide. Both meso-lactide and racemic-lactide are often designated as simply D,L-lactide.

Most reported polydioxaneones are homopolymers, although some attempts have also been reported for the preparation of copolymers between two different dioxaneone monomers. For example, U.S. Pat. No. 2,703,316 by Schneider, issued Mar. 1, 1955, shows two examples of copolymers between different dioxanediones. One copolymer was made from equal parts of glycolide and lactide that is described as being hot pressed into a film. Another copolymer was made from 12 parts of lactide and 2 parts of tetramethylglycolide (3,3,6,6-tetramethyl-1,4-dioxane-2,5-dione). No properties of the latter copolymer were reported and no indication was given that the copolymer could be incorporated into useful product forms.

Due to the expense and difficulty in preparing polydioxaneones, their use has been largely confined to high-value medical applications where bioabsorbable materials are required. Most reported medical applications involve use of the polymers internally in the human body, such as for use as sutures, prosthetic devices, and carriers for the controlled release of pharmaceuticals. Even in the medical field, however, few copolymers between different dioxaneones have been reported, with the exception of copolymers between lactide and glycolide and various copolymers between different optical isomers of lactide, and copolymers of 2-keto-1,4-dioxane with glycolide or lactide. Medical applications involve relatively predictable and constant environmental conditions to which the polymers are subjected during use, i.e., the human body. Therefore, the need to manipulate or modify the properties of polymers used in such medical applications has not been great.

One reference, U.S. Pat. No. 3,636,956 by Schneider, issued Jan. 25, 1972, discloses making filaments that could be useful as sutures from various copolymers using lactide. One example shows polymerization of 44.2 parts of L-lactide and 5.8 parts of the cyclic ester of α-hydroxybutyric acid (3,6-diethyl-1,4-dioxane-2,5-dione). Another example shows 45 parts of L-lactide copolymerized with 5 parts of the cyclic ester of α-hydroxyheptanoic acid (3,6-dipentyl-1, 4-dioxane-2,5-dione). Both copolymers were spun through a 35 mil spinneret and then drawn to form filaments.

Due to the current lack of available landfill space and the concern over environmental contamination, a need exists for polymers that can be used to make degradable plastic products for mass market applications. Little attention has been given, however, to the use of
applications. polydioxaneones for mass-market consumer Such potential mass-market applications include, for example, foam matsrials, molded products, pellet materials, adhesives, laminates, nonwoven materials and films.

Some attempts have been made to make degradable products for mass market applications. U.S. Patent No. 5,076,983 by Loomis et al., issued Dec. 31, 1991, discusses preparation of film materials from certain "polyhydroxy acids," including polymers made from lactide monomers. The film materials of Loomis et al. require the inclusion of external plasticizers.

The use of external plasticizers as required by U.S. Pat. No. 5,076,983, however, may add to the expense and complexity of preparing the materials. As discussed in U.S. Pat. No. 5,180,765 by Sinclair, issued Jan. 19, 1993, such external plasticizers must be intimately dispersed within the polymer composition. Also, some such external plasticizers tend to migrate and segregate from the polymer during processing at elevated temperatures further complicating the manufacture of many useful product forms.

Polymers of the same chemical structure as a polydioxanedione can be prepared by directly polymerizing α-hydroxycarboxylic acids in a condensation polymerization reaction. Such polymers, however, suffer from a low molecular weight. For example, Fukuzaki et al., *Low-Molecular-Weight Copolymers Composed of L-lactic Acid and Various DL-Hydroxy Acids as Biodegradable Carriers,* Makromol. Chem. 190, 2571–2577 (1989), discloses 70/30, molar ratio, of condensation copolymers made from L-lactic acid/D,L-lactic acid, L-lactic acid/D,L-α-hydroxybutyric acid, L-lactic acid/D,L-α-hydroxyisovaleric acid, and L-lactic acid/D,L-α-hydroxyisocaproic acid. As with other reported condensation polymers prepared from α-hydroxycarboxylic acids, however, those polymers were all of low molecular weight, on the order of a few thousand. Such low molecular weights may be adequate for some applications, such as some drug delivery applications as suggested by Fukuzaki et al., but have limited potential for mas-market product applications.

Higher molecular weight polymers have been produced by ring-opening polymerization of dioxanedione monomers. Dioxanediones used as monomers to produce higher molecular weight polymers have traditionally been made from low molecular weight poly-α-hydroxycarboxylic acids by a depolymerization reaction often referred to as "backbiting." These low molecular weight polymers are often referred to as oligomers. The backbiting process is slow and expensive, contributing to the lack of interest in attempting to develop low-cost consumer products for mass-market applications using polydioxanedione polymers.

SUMMARY OF THE INVENTION

The present invention relates to degradable materials comprising polydioxaneone polymers, including nitrogen-containing analogues thereof. In one aspect, polydioxaneone polymers comprise polydioxanediones, including nitrogen-containing analogues thereof. In one aspect, polymers used in making materials of the present invention comprise at least two different dioxaneone-based repeating units, with at least one and more preferably at least two being dioxanedione-based repeating units. Constituent side chains extending, or pendant, from the polymer backbone have a greater number of carbon atoms in second repeating units than in first repeating units. By incorporating such different repeating units and/or by incorporating different proportions of such different repeating unittr into the polydioxaneone, it has been found that properties of the materials of the present invention can be varied. It has been found, for example, that the flexibility required for the materials of the present invention can be effected without resorting to the use of external plasticizers.

In one embodiment, there is a substantially greater proportion, by weight, of first repeating units relative to second repeating units. In one embodiment, first repeating units have a molecular weight less than about 145. In another embodiment, first repeating units comprise repeating units derived from polymerization of lactide. In another embodiment first repeating units comprise repeating units derived from the polymerization of glycolide. In another embodiment, second repeating units result from polymerization of monomers selected from the group consisting of tetramethyl glycolide, the cyclic diester of α-hydroxyisovaleric acid, the cyclic diester of α-hydroxycaproic acid, the cyclic diester of α-hydroxyisocaproic acid, the cyclic diester of α-hydroxyoctanoic acid and combinations thereof. In one embodiment, the total number of carbon atoms in constituents extending from second repeating units in the polymer backbone is at least four and the total number of carbon atoms in constituents extending from first repeating units is at most two. In one preferred embodiment, the number of carbon atoms in constituents extending from second repeating units is at least five. In one preferred embodiment, the materials of the present invention are substantially free of external plasticizer for the polymer.

In one embodiment, second repeating units result from the polymerization of symmetrically substituted dioxaneones, and preferably symmetrically substituted dioxanediones, or from nitrogen-containing analogues thereof. In another embodiment, second repeating units result from polymerization of unsymmetrically substituted dioxaneones, and preferably unsymmetrically substituted dioxanediones, or from nitrogen-containing analogues thereof.

In one embodiment, first repeating units comprise a substantially greater weight percent of the polymer than second repeating units. The polymers used in the present invention vary in physical properties and particularly in molecular weight, depending upon the particular product embodiment. In one embodiment however, polymers of the present invention have weight-average molecular weights of from about 50,000 to about 500,000.

Materials of the present invention are degradable and include molded products, laminates, foams, nonwoven materials, adhesives, coatings, and films, and particularly packaging films for mass-market applications. In one embodiment, physical characteristics of the materials of the present invention are varied, without the use of external plasticizers, by the choice of and the relative amounts of first repeating units and second repeating units in a polymer used to make the materials.

In another aspect, the present invention provides for control of the degradation of materials by various methods. In one particularly preferred embodiment, degradation of the materials made using polydioxaneones, or nitrogen-containing analogues thereof, can be controlled by the choice of and/or the proportion of first repeating units and second repeating units.

In another aspect, the present invention provides for the use of dioxaneone monomers, and preferably dioxanedione monomers, or nitrogen-containing analogues thereof, for preparation of polydioxaneones, which are preferably polydioxanediones, or nitrogen-containing analogues thereof useful in making materials of the present invention. In one embodiment, first monomers have constituents extending from the dioxane ring, or nitrogen-containing analogue ring thereof, that contain fewer carbon atoms than the constituents extending from the dioxane ring, or nitrogen-containing analogue ring thereof, of second monomers. In one embodiment, first monomers have a molecular weight less than about 145. In another embodiment first monomers comprise lactide. In another embodiment, first monomers comprise glycolide. In one embodiment, second monomers axe selected from the group consisting of tetramethyl glycolide, the cyclic diester of α-hydroxyisovaleric acid, the cyclic diester of α-hydroxycaproic acid, the cyclic diester of -hydroxyisocaproic acid, the cyclic diester of α-hydroxyoctanoic acid and combinations thereof. In one embodiment, the total number of carbon atoms in constituents extending from the dioxane ring, or nitrogen-containing analogue ring thereof, of second monomers is at least four and the total number of carbon atoms in constituents extending from the dioxane ring, or nitrogen-containing analogue ring thereof, of first monomers is at most two. In one preferred embodiment, the total number of carbon atoms in constituents extending from the dioxane ring, or nitrogen-containing analogue ring thereof, of second monomers is at least five.

In another aspect, the present invention provides methods for preparing monomers, and particularly dioxanedione monomers, useful for making polymers for the materials of the present invention. In another aspect, the present invention provides methods for preparing polydioxaneones and nitrogen-containing analogues thereof.

In one embodiment, dioxaneone monomers, or nitrogen-containing analogues thereof, are prepared from noncyclic two member, three member, and/or four member oligomers of base molecules such as α-hydroxycarboxylic acids, α-hydroxyamides, and/or salts and other derivative compounds of those acids and amides. In another embodiment, different dioxaneone monomers, or nitrogen-containing analogues thereof, can be prepared individually and then mixed together and polymerized to prepare the polymers useful for manufacturing materials for the present invention. In another embodiment, different dioxaneone monomers, or nitrogen-containing analogues thereof, can be prepared together. In another embodiment unsymmetrically substituted dioxaneones, or nitrogen-containing a analogues thereof, can be prepared for use as monomers.

In another aspect, the present invention relates to reducing waste accumulation. In one embodiment, the rate of degradation of a material may be controlled by varying the type and amount of second repeating units. In another embodiment, hydrolytic degradation occurs at an accelerated rate following disposal relative to the degradation rate during storage and use. In another embodiment, the material degrades at from about 3 months to about 48 months following disposal.

DETAILED DESCRIPTION OF THE INVENTION

The present invention is directed toward various degradable materials comprising hydrolytically degradable, dioxaneone-based polymers, otherwise known as polydioxaneones, or nitrogen-containing analogues thereof. A nitrogen-containing analogue of a polydioxaneone, as used herein, refers to a polymer in which one or more of the normal oxygen linkages of a polydioxaneone are instead occupied by nitrogen linkages. Nitrogen-containing analogues of dioxaneones, as used herein, refers to a ring compound in which nitrogen occupies one or more of the positions normally held by oxygen in the dioxane ring. In one aspect, the present invention provides certain degradable materials including molded products, laminates, foams, nonwoven materials, adhesives, coatings, and films, and particularly packaging films. In another aspect, the degradation rate of materials can be controlled, such as by the choice and/or relative proportions of comonomers. In another aspect, polydioxaneones used in materials of the present invention can be made from dioxaneone monomers. In another aspect, dioxaneone monomers, or nitrogen-containing analogues thereof, can be made directly from noncyclic esters, or ester amides, of α-hydroxycarboxylic acids and/or esters, salts and/or amides thereof. Although the discussion contained herein primarily refers to dioxaneones and materials made from polydioxaneones, the same principles are also applicable to nitrogen-containing analogues of dioxaneones and polydioxaneones. Also, dioxaneone and polydioxaneone are sometimes written in the literature as dioxanone and polydioxanone, respectively. As used herein, the spellings are interchangeable.

Internally Modified Polymer

Materials of the present invention, which involve internally modified polymer compositions, comprise polymers, generally referred to herein as polydioxaneones, having first repeating units of the formula

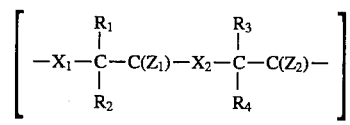

where,
independently for each such first repeating unit:
$X_1$ and $X_2$ are independently O or NR' and R' is independently H, hydrocarbyl, substituted hydrocarbyl or a hydrocarbyl derivative, including heteroatom containing constituents; $R_1$, $R_2$ and $Z_1$ combined have at most one carbon atom;
$R_3$, $R_4$ and $Z_2$ combined have at most one carbon atom; and $Z_1$ and $Z_2$ are each independently one or more constituent group (e.g., hydrogen, hydrocarbyl, oxygen, etc.) extending from the polymer backbone chain and being covalently bonded to a tetravalent carbon atom in the polymer backbone chain, at least one of $Z_1$ and $Z_2$ being an oxygen that forms a carbonyl group with the associated carbon atom in the polymer backbone chain;
and having second repeating units of the formula

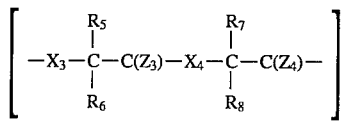

where, independently for each such second repeating unit:
$X_3$ and $X_4$ are independently O or NR' and R' is independently H, hydrocarbyl, substituted hydrocarbyl or a hydrocarbyl derivative, including heteroatom containing constituents; $R_5$, $R_6$, $R_7$ and $R_8$ combined have at least four carbon atoms; and $Z_3$ and $Z_4$ are each independently one or more constituent group (e.g., hydrogen, hydrocarbyl, oxygen, etc.) extending from the polymer backbone chain and being covalently bonded to a tetravalent carbon atom in the polymer backbone chain, at least one of $Z_3$ and $Z_4$ being an oxygen that forms a carbonyl group with the associated carbon atom in the polymer backbone chain.

First and second repeating units can be present in the polymer in any fashion; including in random, alternating, and block configurations. As used herein, hydrocarbyl refers to any constituent group having only hydrogen and carbon atoms, including aliphatic, aromatic, cyclic, noncyclic, saturated, and unsaturated constituents.

Polymers of the materials of the present invention are generally referred to herein as polydioxaneones. It will be recognized, however, that when any of $X_1$, $X_2$, $X_3$ or $X_4$ are NR, then the polymer may contain amide linkages characteristic of polyamino acids. As used herein, polydioxaneone generally refers to polymers having repeating units characteristic of monomers of dioxaneones, or the nitrogen-containing analogues thereof. Dioxaneone as used herein is in a general context to refer to a class of compounds having a dioxane ring, or a nitrogen-containing analogue ring thereof, and having one or more carbonyl oxygens pendant from that ring. Preferably, at least one of $X_1$ and $X_2$ and at least one of $X_3$ and $X_4$ is oxygen. When all of $X_1$, $X_2$, $Z_1$ and $Z_2$ are oxygen, the first repeating unit would be characteristic of a repeating unit derived from a dioxanedione monomer, a particular type of dioxaneone having two carbonyl groups. Likewise, when all of $X_3$, $X_4$, $Z_3$ and $Z_4$ are oxygen, the second repeating unit would be characteristic of polymerization of a dioxanedione. Specific examples of dioxanediones include, for example, lactide, glycolide and other cyclic diesters of α-hydroxycarboxylic oxides. Polymers having repeating units characteristic of dioxanedione monomers can be referred to more specifically as polydioxanediones. As used herein, polydioxanedione includes nitrogen-containing analogues, having nitrogen rather than oxygen, as one or more of $X_1$, $X_2$, $X_3$ and $X_4$ in the polymer backbone. Likewise, as used herein, dioxanedione includes nitrogen analogues, such as, for example, dilactams.

In one embodiment, first repeating units have the formula

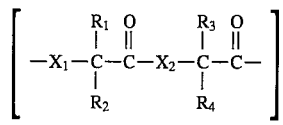

where, independently for each such first repeating unit:
$X_1$ and $X_2$ are independently O or NR' and R' is independently H or hydrocarbyl; $R_1$ and $R_2$ combined have at most one carbon atom; and $R_3$ and $R_4$ combined have at most one carbon atom.

In one embodiment, second repeating units are of the formula:

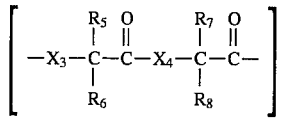

where, independently for each such second repeating unit:
$X_3$ and $X_4$ are independently O or NR' and R' is independently H or hydrocarbyl; and $R_5$, $R_6$, $R_7$ and $R_8$ combined have at least four carbon atoms.

In one embodiment, the materials of the present invention comprise a polymer having one or more repeating units in addition to the first and second repeating units. For example, such additional repeating units could be derived from additional dioxaneone monomers or from other monomers capable of polymerization with dioxaneones, including lactones, such as β-butyrolactone, γ-butyrolactone, γ-valerolactone, δ-valerolactone, ε-caprolactone, lactams, epoxides, glycols, succinic acid, tartaric acid, mandelic acid, benzylic acid, and others. The polymers could, therefore, be copolymers containing in excess of two comonomers. Particularly preferred as additional repeating units are those representative of polymerization of glycols (also known as dihydric alcohols or diols). For example, blocks of such glycols could be added into a polymer having first and second repeating units by adding the glycols to a reactive bath following polymerization to form the first and second repeating units. Any glycol, such as ethylene or propylene glycol could be used.

The polymers may be plasticized using external plasticizers. In a preferred embodiment, however, the polymer is substantially free of any external plasticizer. Rather, the first repeating units and the second repeating units are selected to provide the desired physical properties, thereby eliminating the need for external plasticizers and associated costs and complexities of using the same. Not to be bound by theory, it is believed that second repeating units impart flexibility into the composition by breaking up the structural regularity otherwise imparted by the first repeating unit, thereby providing the possibility for an amorphous polymer with a substantial amount of internal freedom.

In one embodiment, first repeating units comprise greater than 50 weight percent of the polymer, preferably from about 50 weight percent to about 99 weight percent of the polymer, more preferably from about 80 weight percent to about 99 weight percent of the polymer still more preferably from about 90 weight percent to about 99 weight percent of the polymer, and most preferably from about 90 weight percent to about 97 weight percent of the polymer.

In one embodiment, the second repeating units comprise less than 50 weight percent of the polymer, preferably from about 1 weight percent to about 50 weight percent of the polymer, more peferably from about 1 weight percent to about 20 weight percent of the polymer, still more preferably from about 1 weight percent to about 10 weight percent of the polymer, and most preferably from about 3 weight percent to about 10 weight percent of the polymer.

In one embodiment, the first repeating units have a molecular weight less than about 145. Such first repeating units could be derived, for example, from polymerization of lactide and/or glycolide monomers.

In one embodiment, second repeating units are derived from polymerization of tetramethyl glycolide. In another embodiment, second repeating units are derived from polymerization of the cyclic diester of α-hydroxyisovaleric acid. In another embodiment, second repeating units are derived from polymerization of the cyclic diester of α-hydroxycaproic acid. In another embodiment, second repeating units are derived from polymerization of the cyclic diester of α-hydroxyisocaproic acid. In yet another embodiment, the second repeating units are derived from polymerization of the cyclic diester of α-hydroxyoctanoic acid. It should be recognized that the hydrocarbyl side chain in the branched isomers of α-hydroxyisovaleric acid and α-hydroxyisocaproic acid could take one of multiple branched forms. In one embodiment, such branched isomers comprise a mixture of two or more of those possible for such an iso-acid compound.

In one particularly preferred embodiment, first repeating units are derived from polymerization of lactide and second repeating units are derived from polymerization of monomers selected from the group consisting of tetramethyl glycolide, the cyclic diester of α-hydroxyisovaleric acid, the cyclic diester of α-hydroxycaproic acid, the cyclic diester of α-hydroxyisocaproic acid, the cyclic diester of α-hydroxyoctanoic acid, and combinations thereof.

The constituents $R_1$, $R_2$, $R_3$, $R_4$, $R_5$, $R_6$, $R_7$, and $R_8$ may be any organic constituents, but preferably are hydrocarbyl or hydrogen. R' is preferably hydrogen or hydrocarbyl.

In one embodiment, at least one of $R_5$ and $R_6$ and at least one of $R_7$ and $R_8$ are hydrocarbyl radicals having from two to three carbon atoms. In another embodiment, at least one of $R_5$, $R_6$, $R_7$ and $R_8$ is a hydrocarbyl radical having from 4 carbon atoms to about 24 carbon atoms, preferably from 4 carbon atoms to about 16 carbon atoms, and more preferably from 4 carbon atoms to about 10 carbon atoms. In one preferred embodiment, the total number of carbon atoms in $R_5$, $R_6$, $R_7$, and $R_8$ combined is at least 5, and more preferably is from 5 to about 12. In one embodiment, at least one of $R_5$ and $R_6$ and at least one of $R_7$ and $R_8$ is a saturated hydrocarbyl radical. In a preferred embodiment, $R_5$, $R_6$, $R_7$ and $R_8$ are each independently either hydrogen or hydrocarbyl.

In one embodiment, one of $R_5$ and is isopropyl and the other is hydrogen, and one of $R_7$ and $R_8$ is isopropyl and the other is hydrogen. In another embodiment, one of $R_5$ and $R_6$ is propyl and the other is methyl, and one of $R_7$ and $R_8$ is propyl and the other is methyl.

In one embodiment, the constituents $R_5$ and $R_6$ are the same as the constituents $R_7$ and $R_8$, such as would be the case if the second repeating units were derived, for example, from a symmetrically substituted dioxanedione. In another embodiment, the total number of carbon atoms in $R_5$ and $R_6$ combined is different than the number of carbon atoms in $R_7$ and $R_8$ combined, such as would be the case, for example, if the second repeating units were derived from an unsymmetrically substituted dioxanedione.

In one embodiment, the polymers used for the materials of the present invention have a weight-average molecular weight of greater than about 30,000, preferably greater than about 70,000 and more preferably greater than about 100,000. Although the desired molecular weight of the polymer will depend upon the specific product embodiment, as discussed below, one generally preferred range is a weight-average molecular weight of from about 50,000 to about 500,000, more preferably from about 100,000 to about 500,000, and still more preferably from about 150,000 to about 250,000.

Materials

As discussed above, the present invention is directed to various materials which include polydioxaneones, or nitrogen-containing analogues thereof, as previously described. The various materials of the present invention have varying chemical and physical characteristics that are relevant to their intended uses. The materials of the present invention include the following types: films, molded products, laminates, foams, nonwoven materials, adhesives and coatings.

Film material of the present invention is made from a polydioxaneone as described above, and preferably from a polydioxanedione, or from a nitrogen-containing analogue. The term film, as used herein, refers to a material type which is a film in its final product configuration and does not refer to intermediate source materials which are subsequently processed into nonfilm products. The term film includes products that are commonly identified as films that have thicknesses of less than about 20 mils, and also includes materials which may also be termed sheets, including materials with thicknesses up to about 50 mils. Such films can be prepared to simulate the properties of several common plastics, such as those made from polyethylenes, polystyrenes, and vinyls. The desired molecular weight distribution for each application is achieved by adjustment of the polymerization conditions and by post-polymerization processing. Choices and percentages of first repeating units and second repeating units of the polymer affect flexibility and other final characteristics, acceptable processing temperature, intended service temperature, and degradation rate of-the product.

Such films can be produced by a variety of processes. For example, films can be prepared by compression molding processes. Suitable films can also be prepared by extrusion processes, including blown film processes, melt-extruded casting, and by casting solutions of the polymer composition and then recovering the solvent.

Thermal annealing and quenching are two methods for controlling the morphology of the film to emphasize selected properties. Quenching as used herein indicates that the temperature of a material is dropped rapidly to prevent extensive crystallization of the polymer. Crystallization of polymers is frequently a relatively slow process, requiring from minutes to hours to fully accomplish.

When crystallization is desired, the temperature is held above the glass-transition temperature, $T_g$, for some time to allow the molecules to order themselves into extensive crystalline lattices. This process is called annealing.

When cooled rapidly from an amorphous melt, the polymer does not have time to substantially crystallize and remains largely amorphous. The time required to quench depends on the thickness of the sample, its molecular weight, melt viscosity, compositions, and $T_g$. Thin films obviously cool very quickly because of their high surface-to-volume ratio while thicker films cool more slowly. Polydioxaneones, and particularly polydioxanediones, or nitrogen-containing analogues, having a lower relative proportion of second repeating units order more easily and crystallize more quickly than those having a higher relative proportion of second repeating units.

Polymers with bulky side groups may crystallize if some level of structural regularity (including stereo regularity) with respect to the side groups occurs. Generally, however, polymers having larger and/or more bulky constituents for one or more of $R_5$, $R_6$, $R_7$ and $R_8$ order less easily and crystallize less quickly than those having smaller and/or less bulky constituents. For example, a butyl constituent, extending as a pendant group from the polymer backbone, would tend to interfere less with crystal development than a hexyl constituent in the same location, and a butyl and a hexyl constituent would each tend to interfere to a greater degree than a methyl group.

Quenching to an amorphous state requires that the polymer or copolymer in an amorphous melt is rapidly cooled from its molten state to a temperature below its $T_g$. Failure to cool rapidly allows spherulitic crystallinity to develop, that is, crystalline domains of a size from submicron to micron. Spherulitic crystallinity tends to scatter light, making the polymer specimens opaque. These spherulitic crystalline forms have improved stability to heat distortion. Such spherulitic crystallinity is often called short range order-long range disorder since the spherulitic crystals domains are separated from one another by amorphous regions. Such crystallites can, however, act as pseudo crosslinks to maintain dimensional stability above the $T_g$ but below the melting point. In one embodiment, film materials of the present invention are less than about 20 percent crystalline.

Stability to heat distortion can also be obtained by orienting an amorphous polymer at a temperature above its $T_g$ and below its melting point. Polymer molecules are physically stretched to allow some long range ordering and, if desired, the polymers can then be "heat set" to permit the ordering to continue through annealing. The amorphous polymer can thereby crystallize into a different order, called long range order-short range disorder. Transparency and resistance to heat distortion are favored.

Films of the present invention can be oriented or unoriented and can be shrinkable or nonshrinkable. As discussed, orientation refers to stretching a film in one direction which allows for alignment and ordering of the polymer molecules along the direction of stretching. The stretching can be two or more times the original length of film in the direction of stretching. Orientation can be uniaxial, which is typically in the direction the film travels as it is processed. Alternately, orientation can be biaxial which is typically orientation both in the direction the film travels as it is processed and in a second direction transverse to the first. Orientation is typically conducted at a film temperature above the $T_g$ of the film and below the melting point. Biaxially oriented films are useful as shrinkable films in shrink wrap packaging.

Biaxially oriented films can be made nonshrinkable by heat setting the films. To heat set oriented films, films are restrained at the dimensions to which they have already been stretched and are subjected to a temperature that is above the $T_g$ and below the melting point. This procedure allows internal tension in the film to relax and upon cooling the film is substantially nonshrinkable.

As noted above, films of the present invention can be prepared having a variety of product characteristics. For example, such films can have polystyrene-like properties, low density polyethylene-like properties, high density polyethylene-like properties, polypropylene-like properties and polyvinyl chloride-like properties.

Polystyrene-like films of the present invention typically are transparent, colorless and semicrystalline, and have a weight-average molecular weight from about 50,000 to about 500,000. Polystyrene-like films typically have a heat distortion temperature from about 54° C. to about 61° C.; have a tensile strength of from about 6,000 psi to about 8,000 psi; Shore D hardness of from about 80 to about 90; elongation to break of from about 2% to about 4% and elastic modules of greater than about 250,000 psi. They typically can degrade under ambient conditions in from about 6 months to about 24 months.

As used herein, a material is transparent if it has a transmittance of greater than about 85% of the visible light spectrum and also preferably, has haze of less than about 10% as measured by a Gardner IHaze Meter. As used herein, a material is substantially colorless if it measures from about zero to about one on the Gardner Scale, or if it measures from about one to about ten on the yellowness index.

Low density polyethylene-like film materials of the present invention are sometimes transparent, are typically colorless, and do not typically exhibit spherulitic crystallinity. They typically have a weight-average molecular weight of from about 50,000 to about 500,000; a heat distortion temperature of from about 32° C. to about 40° C.; tensile strength of from about 1,500 psi to about 3,000 psi; Shore D hardness of about 50; an elongation to break of about 150% to about 1,200%; and elastic modules of from about 10,000 psi to about 50,000 psi. They typically can degrade under ambient conditions in from about 3 months to about 48 months and preferably from about 6 months to about 36 months.

High density polyethylene-like materials of the present invention are sometimes transparent, typically colorless, and usually crystalline. They are sometimes translucent. They typically have a weight-average molecular weight of from about 50,000 to about 500,000; a heat distortion temperature of from about 40° C. to about 90° C.; tensile strength of from about 2,500 psi to about 4,000 psi; Shore D hardness of from about 50 to about 60; an elongation to break of from about 50% to about 500%; and an elastic modules of from about 50,000 psi to about 125,000 psi. They typically can degrade under ambient conditions in from about 6 months to about 48 months, and preferably from about 6 months to about 36 months.

Polypropylene-like films of the present invention are sometimes transparent and are usually crystalline. They are often translucent and may be colorless. They typically have a weight-average molecular weight of from about 50,000 to about 500,000; a heat distortion temperature of from about 50° C. to about 120° C.; a tensile strength of from about 4,000 psi to about 6,000 psi; a Shore D hardness of about 70; an elongation to break of from about 100% to about 600%; and an elastic modules of from about 125,000 psi to about 200,000 psi. They typically degrade under ambient conditions in from about 3 months to about 36 months.

Polyvinyl chloride-like films of the present invention are sometimes transparent and are usually not crystalline. They may or may not be colorless. Fillers may be used to provide the desired optical properties, such as color. They can have a wide range of properties with weight-average molecular weight of from about 50,000 to about 500,000; $T_g$ of below room temperature to about 100° C.; tensile strength of from about 300 psi to about 5,000 psi; Shore D hardness of from about 10 and to 90; elongation to break of from about 5% to about 500%; and elastic modules of from about 500 psi to about 250,000 psi. They typically can degrade under ambient conditions in from about 3 months to about 36 months.

Film materials of the present invention can be made into a wide variety of product types. For example, a particularly advantageous film material of the present invention is in the form of a packaging film. As used herein, packaging film refers to material used to package consumer goods either in a film form or in laminate form, such as a laminate to paper or paperboard. In one embodiment, the packaging film is a thermoplastic of a thickness less than about 20 mils. The film may be used for the purpose of containing, displaying, sealing, or protecting the contents of the package. The film may be used alone or in conjunction with other materials. Preferably, packaging films of the present invention are transparent and substantially colorless. Further, film materials of the present invention can be made into other product types, such as garbage Shelf life is one important consideration for materials of the present invention. As used herein, shelf life refers to the length of time that the package form must be functional and is timed from the manufacture of the package to final disposal by the consumer. Thus, a typical material must be stable from package manufacture, through package use, distribution and sale, and up to the time of package disposal. This stability must encompass mechanical integrity and strength, package attractiveness such as film clarity or scratch resistance, barrier effectiveness, and other use-specific features. Shelf life is then a function of the use.

The material must also endure through several different physical environments such as extreme variations in temperature, humidity, and to some extent pressure as the packaging materials are stacked in raw materials, finished goods or distribution inventories. In some instances, the material may have to be stable in the presence of weak acids or bases or other chemical environments.

Materials of the present invention can be tailored to the requirements of a particular shelf life through the variation of choice of and percentage composition of the polydioxaneones. Such tailoring may be accomplished by incorporation into a copolymer all of the desired repeating units or may be accomplished by blending different polydioxaneones.

In one embodiment, composition of the polydioxaneones used in materials of the present invention are varied by use of two to four different polydioxaneones, and preferably two to four polydioxanediones, in varying amounts to increase the stability of the polymer in extremes of environment ranging from wet, cold beverage packaging (which requires a package with a high wet strength) to dry, warm distribution channel environments. In another embodiment, polydioxaneones are plasticized with external plasticizers or blended with other additives to enhance stability throughout the product's shelf life. Preferably, however, polydioxaneones used for materials of the present invention are substantially in the absence of external plasticizers. One particularly useful addition is an antioxidant. Other additives that could be used include fillers, colorants (both dyes and pigments), flame retardants, anti-static agents, fragrances, ultraviolet stabilizers, and other stabilizers.

Another type of material of the present invention includes various mold products. Molded products can be made by a variety of processes, including blow molding, injection molding and thermoforming. Blow molding is employed to make hollow shapes, especially packaging containers. In the extrusion embodiment of this process, a parison is made and then expanded to the walls of the mold cavity. The degradable polymer composition is tailored to meet extrusion blow molding processing requirements by adjusting the ratio of first repeating units to second repeating units and/or adjusting the molecular weight of the polymer product. These processing requirements are reconciled with the end use requirements with regard to shelf life, strength, speed of onset of degradation, barrier properties, and other parameters. Weight-average molecular weights of over 50,000 and as high as 500,000 are desirable for these applications.

Injection molding of thermoplastics is accomplished by melting the thermoplastic composition and transferring it into a mold cavity where it solidifies to conform to the shape of the mold. Injection molded products require little or no mechanical work before they are fabricated with other parts into an end use product. Injection molded products of the present invention are sometimes transparent. They typically have a weight-average molecular weight of from about 50,000 to about 120,000; a heat-deflection temperature of greater than about 70° C.; a tensile strength of greater than about 3,000 psi; a Shore D hardness of from about 50 to about 90; an elongation to break of from about 2% to about 25%; and an elastic modules of from about 100,000 psi to about 400,000 psi. They typically can degrade under ambient conditions in from about 3 months to about 36 months.

The materials of this invention are highly suitable for injection molding because their melting points and morphology can be tailored in many different ways. The melt rheology of the materials can be adjusted to tailor the melt viscosity, shear dependence, heat-deflection temperatures, crystallization temperature, and other processing requirements. The molecular weights and distribution of molecular weight are commonly adjusted to accommodate flow- and cycle-time requirements. Choice of and percentage of first repeating units and second repeating units can also be varied. Because the economics of injection molding usually necessitates short cycle times, relatively low weight-average molecular weights (less than 120,000) are preferred.

Thermoforming is a branch of molding that uses films or sheets of thermoplastic. Because the materials of this invention are especially easy to convert to film or sheet form that have excellent transparency, they are excellent candidates for thermoforming. The sheet is eated to the temperature at which the polydioxaneone is quite flexible and is then subjected to vacuum or positive pressure to form the sheet about a mold to produce a desired shape.

Molded products can include a number of different product types including, for example, disposable tableware, ammunition cartridge shells, single use camera bodies and parts, bottle-like packaging containers, single use food containers and various thermoforms.

Other material types of the present invention include laminates and coextrudates. Film laminates and coextruded films are composite materials in which each layer provides functional utility that complements the rest of the structure. The polydioxaneone, or nitrogen-containing analogue, materials of this invention provide degradability, in addition to such functions as strength, printability, and high transparency. The other layers in the laminate or coextruded structure can provide temporary protection against moisture or abrasion so that the onset of degradation is delayed until after the desired shelf-life period has passed. The other layers may also provide essential electrical or other functions that require the layer to be nondegradable. Adverse environmental impacts can be reduced, however, by using the polymers, as dascribed previously, for most of the weight of the product.

Laminating resins are another material of the present invention and can be used as a tie-layer between dissimilar surface layers. For example, many packaging materials are prepared using a laminating layer between so-called clayboard, boxboard, or cardboard and outer layers of thermoplastic films. Such laminated materials, for example, have layers which provide various features, such as structural stability, gas permeability, decoration or moisture exclusion.

A polymer of the present invention can be used, for example, as a transparent outer protective coating for such a laminated product, and/or to provide a laminating layer or tie-layer. A particular advantage of a polydioxaneone as a laminating resin is that as it degrades it enhances the separation of the bonded layers, which can be advantageous in processes for recycling of laminated materials.

Laminating resins and coextrudates of the present invention typically are not crystalline. Thus, laminated paper products can be more easily recycled as the polydioxaneone would degrade quickly in a typical paper recycling process. They typically have a weight-average molecular weight of from about 500 to about 5,000; a $T_g$ below about room temperature; a Shore D hardness of about 0.5; an elongation to break of greater than about 300%; and an elastic modules of less than about 1,000 psi. They typically can degrade under ambient conditions in from about 1 month to about 3 months.

A further material type of the present invention includes foams. Foamed thermoplastics have large markets in food packaging. The materials of this invention are good candidates for use in these applications because they can be melted to a high-viscosity material that can be foamed with such gases as carbon dioxide or nitrogen for foam extrusion. The viscosity of the melt can be optimized by control of molecular weight, molecular weight distribution, and/or by modifier content. Typically, the polymer will have a molecular weight of greater than about 300,000 for foam extrusion. The ability to vary the proportion and type of first repeating units and second repeating units are especially desirable for this foam application to ensure that the desired elastic bubble is attained in the foamed product. The solubility (under pressure) of carbon dioxide in the polymers of this invention can be exploited to control the pore sizes of bubbles that are produced after cooling.

Foam materials of the present invention typically are semicrystalline and not transparent. They typically have a weight-average molecular weight of from about 50,000 to about 500,000; and a heat distortion temperature of greater than about 50° C. They typically can degrade under ambient conditions in from about 3 months to about 36 months.

A further material of the present invention includes spun-bonded nonwoven material. The term "spun-bonded nonwoven" refers to material that has been prepared by extruding a filament through a spinnerette onto a flat cooled surface in an irregular pattern to form a relatively uniform sheet which is not in a woven pattern. Spun-bonding requires adherence to a limited range of melt viscosities so that roving spinnerettes can deliver the appropriate amount of material to the cooled surface. The detailed response of the polymer melt to quenching is also a sensitive processing parameter. Such nonwoven materials typically have high strength characteristics and can be used for envelopes, towels, cloth wipes, fabrics, medical gowns, lab coats, and other similar materials. The polydioxaneone of this invention can be optimized to meet the processing requirements by manipulation of many variables, including control of molecular weight and molecular weight distribution and selection and relative amounts of different dioxaneone comonomers.

A further product type of the present invention includes adhesives. The polymer compositions of this invention have considerable utility as adhesives because they can be hot-melt or solvent-based products. Also, their polarity provides an advantage in many adhesive applications. The choice and proportion of first repeating units and second repeating units and the molecular weight distribution of a polymer can affect the melting point of the hot melt and its morphological behavior during tackifying and hardening.

The polymers to be used in adhesives of the present invention range widely in composition and molecular weight, depending on the specific type of adhesive and the specific application. The surface properties of substrates to be bonded are of great importance in the choice of polymer.

Adhesives of the present invention may be, but typically are not, transparent. They typically have a weight-average molecular weight of from about 5,000 to about 200,000; and a $T_g$ of from about room temperature to about 100° C. Depending on end-use temperatures and whether an adhesive is structural—or pressure-sensitive, the adhesive can be rigid or flexible and can vary with respect to properties as mentioned previously in discussing laminating resins and film types.

A further material type of the present invention includes various coatings. Unlike some films, moldings and foams, coatings do not have to be strong enough to be self-supporting. Therefore, an extremely wide range of the polymer compositions of this invention can be employed for coating use. The degradability aspect allows the coating to be a temporary protection of the underlying substrate against abrasion or other harm. The coating can serve many of the functions of a film, especially as a temporary printing surface so that the label of a container is among the first parts of a package to degrade. Polydioxaneone materials print well due to their polarity. Coatings can be applied to a variety of other materials including paper, metals, plastics, wool, and natural and synthetic fibers.

The coating can serve as a binder to incorporate pigments onto writing papers. Pigments are easily accepted by polydioxaneones of the present invention. This type of usage can facilitate the degradation of the paper substrate by providing an acid environment for cellulose hydrolysis. The coating can also be used in aquatic applications. The nonharmful products of degradation of the materials is useful in protecting marine and fresh waters.

The polymers used in making coatings of the present invention have favorable melt viscosities that allow rapid coating application. Melt viscosity can be controlled by choice of first and second repeating units and/or the ratio of first and second repeating units and/or molecular weight of the polymer. These compositions are thermally stable at temperatures somewhat above their melting points, provided that exposure to moisture is controlled. In addition, coatings of the present invention can be dissolved in solvents and applied as solutions. Emulsion coatings are also possible, with due consideration for the effects of water in an emulsion on the shelf life of the coating.

Generally, the polymers to be used in coatings can have a lower molecular weight and less crystallinity than those that are to be used in films. Thus, weight-average molecular weights may range from about 10,000 to about 100,000, and are preferably greater than about 50,000.

Although the materials of the present invention are environmentally degradable, they also can be treated by other disposal systems. In particular, they can be incinerated in facilities that burn other plastic wastes. Also, due to their high oxygen content, they can aid in promoting complete combustion of other plastics with which they may be burned. They also can be recycled with other hermoplastics by blending.

Additional information concerning suitable processes for preparing compositions of the present invention can be found in U.S. Pat. No. 5,180,765 by Sinclair issued Jan. 19, 1993 and in co-pending U.S. application Ser. Nos. 07/579, 465 by Sinclair filed Sep. 6, 1990 and 07/950,854 by Sinclair et al. filed Sep. 22, 1992, all of which are incorporated herein by reference in their entirety.

Degradation of Materials

The materials of the present invention comprise polydioxaneones, including polydioxanediones as previously discussed, and nitrogen-containing analogues thereof, which are degradable as mentioned previously. As used herein, "degradable" refers to the capacity of a polymer molecule to decompose to smaller environmentally innocuous molecules. Such degradation or decomposition can be by various chemical mechanisms. For example, degradation can be by hydrolysis, whereby the polymer chain is severed by water reacting with a polymer to form two or more smaller molecules. Degradation can also be by biodegradation such as when molecules are enzymatically broken down by microorganisms. Once the polymer has degraded significantly, the degradation products can be a food source for microorganisms.

In one embodiment, the polymers of the present materials are further characterized as being degradable within a time frame in which materials from which products may be made, after use, can either be readily recycled by decomposition of the polymer or, alternatively, if the polymer material is disposed of in the environment, such as in a landfill, the polymer degrades quickly enough to avoid significant accumulation of solid waste. Such accumulation is, at least, significantly less than that resulting from nondegradable products.

The degradation characteristics of the polymer in the present materials depend in large part on the type of material being made with the polymer. Thus, the polymer needs to have suitable degradation characteristics so that when processed and produced into a final material, the material does not undergo significant degradation until after the useful life of the material. Therefore, different product embodiments of the present invention will have different degradation characteristics as previously discussed.

The timing of degradation of the materials can be evaluated by accelerated short-term testing under which materials are exposed to harsh conditions. In one embodiment, a test for degradability is an accelerated short-term test in which materials are subjected to a temperature of 95° F. (35° C.) and 95% humidity. Under these sample conditions a test sample of material which is in the configuration of a 1–3 mil film could be considered to be degradable if, for example, it becomes sticky to the touch, cloudy or opaque and embrittled in less than about three months. In another embodiment, a test for degradability, is whether the material which is in the configuration of a 1–3 mil film has a tensile strength loss or a molecular weight loss under the accelerated test conditions, as previously described, of at least about 90% in less than about six months.

Hydrolytic degradation rates for various materials of the present invention can be controlled in a number of ways. In a preferred embodiment, the rate of hydrolytic degradation is controlled by the selection of and the relative amounts of first repeating units and second repeating units in a polymer. For example, in a similar structure, larger and/or bulkier hydrocarbyl constituents for $R_5$, $R_6$, $R_7$ and/or $R_8$ may speed the rate of degradation compared to smaller and/or less bulky constituents that do not permit water to as easily invade the polymer matrix and to access hydrolytic degradation sites in the polymer. Therefore, for example, a hexyl group extending from the polymer backbone may speed degradation relative to a methyl group at the same location. Such a result is particularly surprising because it would be anticipated that a bulkier constituent, such as a hexyl group, would impede degradation relative to a methyl group at the same location due to the higher hydrophobicity of the hexyl group. Surprisingly however, the bulkier group, even through more hydrophobic, may permit faster degradation by permitting water to more easily invade into interstitial space of the polymer matrix and to thereby access hydrolytic degradation sites on a polymer chain. Bulky constituents, if not tightly packed with the rest of the polymer chain in the polymer matrix, may increase hydrolytic degradability by increasing the interstitial free volume which provides easier access of water molecules to ester, or amide, linkages in the polymer. Also, proper selection of first repeating units and second repeating units avoids regularity of structure that can result in degradation rates that are too slow. This may be the case for highly crystalline polymers such as a L-lactide homopolymer.

In another embodiment, however, inclusion of second repeating units may slow degradation of a material relative to a comparison material made from a polymer not having the second repeating unit. This may be the case, for example, when the inclusion of second repeating units does not appreciably increase the amount or character of interstitial free volume in the polymer matrix available for access by water. In such a case, the increasingly hydrophobic character of the second repeating unit will slow degradation due to the hydrophobicity of the second repeating unit.

In one embodiment, materials of the present invention take at least about 20% longer to degrade than the same material if made using the same polydioxaneone, except without the second repeating units. Preferably, the time to degrade is at least about 100% longer and more preferably is at least about 200% longer by inclusion of such second repeating units.

Not to be bound by theory, it is believed that more numerous and/or larger hydrocarbyl or substituted hydrocarbyl constituents extending from second repeating units of the polydioxaneone chain can interfere with the ability of water to access ester, or amide, bonds of the polymer backbone to accomplish hydrolytic degradation, given a relatively constant ability for water to access hydrolytic degradation sites inside the polymer matrix. The second repeating units therefore, appear to add hydrophobicity to the polydioxaneone, especially when they contain hydrocarbyl constituents, and particularly when they contain saturated hydrocarbyl constituents, that extend from the polymer backbone.

Various other degradation strategies that can be used with the polydioxaneone materials of the present invention are discussed in detail in co-pending, commonly assigned U.S. patent application Ser. No. 07/949,675 by Sinclair et al. filed on Sep. 22, 1992, which is incorporated herein in its entirety. Any of the degradation control strategies of the present invention can be combined in any combination with any of the materials of the present invention.

For example, one method of controlling the rate of hydrolytic degradation of the materials is to control acid or base catalyzed degradation of the polymer. Not to be bound by theory, it is believed that polydioxaneones, including polydioxanediones, and nitrogen-containing analogues, as discussed, hydrolytically degrade by two mechanisms: random scission within the polymer and backbiting of the terminal hydroxyl ends of the polymer.

In addition, carboxyl ends apparently promote degradation both by polarizing ester bonds and by providing acid groups that increase (i.e., accelerate) the rate of hydrolysis. Also, it is believed that free carboxyl groups are surrounded by shells of water which promote degradation. As more carboxyl end groups are formed during hydrolysis, there are additional acid groups which can trap and accumulate water.

Reactive carboxyl and/or hydroxyl ends may be responsible for enhancing degradation during melt processing and during use and disposal stages of a product's life. Thus, in one embodiment, endcapping the reactive hydroxyl and/or carboxyl groups reduces the rate of degradation.

Additionally, other strategies can be used to control degradation based on acid or base catalysis of degradation. For example, materials can be produced which include encapsulated acid or base compounds which, upon release, rapidly promote degradation. For example, acid or base compounds can be microencapsulated in degradable polymeric material or abrasion prone material so that subsequent to use, after being discarded, the microcapsules will break down and release acid or base compounds to speed degradation of the entire material.

A further strategy for controlling degradation of materials of the present invention is to change the molecular weight of the polymer. Higher molecular weight material will degrade more slowly, as measured by loss of physical properties such as loss of molecular weight, because each polymeric molecule requires more hydrolytic reactions for total degradation. Higher olecular weights of polydioxanedione can be achieved, for example, by polymerizing from dioxanedione monomers, rather than direct polymerization from α-hydroxycarboxylic acids. Other polymerization techniques for achieving high molecular weights are well known. In addition, cross-linking of polymers achieves effective higher molecular weights and more tightly bound materials that degrade at a slower rate.

A further mechanism for controlling the rate of degradation of materials of the present invention is to change the hydrophobic or hydrophilic nature of the material. The degradation rate of a polymer that is hydrolytically degradable can be reduced by making the material more hydrophobic so that water penetration of the material will be retarded. Incorporation of substantial saturated hydrocarbyl constituents, such as for $R_5$, $R_6$, $R_7$ and $R_8$, extending from the backbone of the polymer, as previously discussed, is particularly effective for producing a material that is substantially more hydrophobic. The rate of degradation can be increased by making the material more hydrophilic. Additionally, the hydrophobic or hydrophilic nature of the material can be modified by physically blending in compounds which are either hydrophobic or hydrophilic to the material without being chemically bound to any of its constituents.

A further strategy for controlling the degradation time of materials of the present invention is to vary the crystalline structure of the polymer in the materials. For polymers which are more crystalline and ordered in their molecular structure, the ability of water to infiltrate and hydrolytically degrade polymers is reduced. Thus, by producing materials which are less crystalline in structure, the rate of degradation will be increased. Materials with a lower $T_g$ also tend to degrade more rapidly.

For example, by incorporating modifiers, such as plasticizers, into a polymer, the crystalline nature of the material will be reduced. Additionally, polymers which are homopolymers are typically more crystalline in nature than copolymers or polymer blends. Further, the crystallinity of the materials, such as films, can be increased by orientation, including uniaxial and biaxial orientation, as described more fully above.

Additionally, materials of the present invention can be coated or laminated with protective layers to exclude water to prevent hydrolytic degradation. For example, a material can be coated with some abrasion prone material which upon being discarded would likely be abraded, thus allowing moisture to infiltrate and hydrolytically degrade the polymer.

A further degradation control strategy is to control the surface area of the material. At higher ratios of surface area to volume, materials of the present invention will degrade more quickly because of greater exposure to environmental moisture. Thus, materials of the present invention can be formed into various product shapes having varying degrees of surface area. Also, degradation after use can be accelerated by increasing the surface area to volume ratio, such as, for example, by shredding films or other product forms.

A further strategy for controlling the rate of degradation of materials of the present invention is to incorporate compounds into the material which have the capacity to absorb and isolate water from the degradable polymer. Such compounds slow the rate of degradation until the capacity for absorbing and isolating water is exceeded. Thereafter, further exposure to moisture allows for unhindered hydrolytic degradation of the polymeric material.

The rate of degradation of certain products can also be controlled by forming product structures having, or capable of inducing, physical stresses on the degradable polymeric material, such as a torsional stress. Such built-in stresses increase susceptibility of the material to degradation.

Another strategy for increasing the rate of degradation of materials of the present invention is to incorporate into the polymer, or to otherwise incorporate into the material, compounds that provide nutrition for microorganisms capable of biodegrading the polymer or hydrolysis degradation products thereof. For example, a polydioxanedione can be hydrolytically degraded to α-hydroxycarboxylic acids, which then can subsequently be biodegraded by a variety of microerganisms. Thus, for example, a polydioxaneone-based material can incorporate a compound which includes nitrogen, phosphate and other salts and metals for the purpose of providing a more available nutritional source for microorganisms, thereby speeding biodegradation. In one embodiment, nitrogen can be supplied by using a nitrogen-containing dioxaneone analogue, as previously described, to prepare the polymer used to make a material of the present invention.

While an important characteristic of the present materials is their degradability, it should be recognized that to be commercially useful, the materials need to be stable, that is, nondegradable for a period of time and under conditions such that they are commercially useful for intended product applications. Representative stability parameters are as discussed previously.

Additional information concerning the control of degradation of materials of the present invention can be found in co-pending U.S. application Ser. No. 07/949,675, as previously discussed.

Monomers

Monomers useful for preparing first repeating units and second repeating units of polymers, from which materials of the present invention are made, can be any monomers that, when polymerized, result in the first and second repeating units respectively. Such monomers could be, for example, α-hydroxycarboxylic acids or esters, salts or amides thereof. Preferably, however, the monomers used to prepare the first repeating units and second repeating units are cyclic compounds, such as dioxaneones or nitrogen-containing analogues thereof. Preferably, first monomers result in first repeating units upon polymerization and second monomers result in second repeating units upon polymerization.

In one embodiment, cyclic compounds used as monomers to prepare polymers of the present materials comprise first monomers of the formula

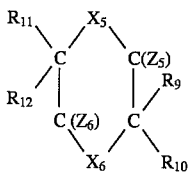

where,
independently for each such first monomer:
$X_5$ and $X_6$ are independently O or NR' and R' is independently H, hydrocarbyl, substituted hydrocarbyl or a hydrocarbyl derivative, including heteroatom containing constituents; $R_9$, $R_{10}$ and $Z_5$ combined have at most one carbon atom;
$R_{11}$, $R_{12}$ and $Z_6$ combined have at most one carbon atom; and $Z_5$ and $Z_6$ are each independently one or more constituent group (hydrogen, hydrocarbyl, oxygen, etc.) extending from the ring and being covalently bonded to a tetravalent carbon atom in the ring, at least one of $Z_5$ and $Z_6$ being an oxygen that forms a carbonyl group with the associated carbon atom in the ring;
and comprise second monomers of the formula

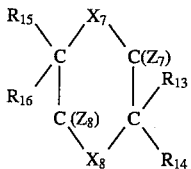

where,
independently for each such second monomer:
$X_7$ and $X_8$ are independently O or NR' and R' is independently H, hydrocarbyl, substituted hydrocarbyl or a hydrocarbyl derivative, including heteroatom containing constituents; $R_{13}$, $R_{14}$, $R_{15}$ and $R_{16}$ combined have at least four carbon atoms; and $Z_7$ and $Z_8$ are each independently one or more constituent group (hydrogen, hydrocarbyl, oxygen, etc.) extending from the ring and being covalently bonded to a tetravalent carbon atom in the ring, at least one of $Z_7$ and $Z_8$ being an oxygen that forms a carbonyl group with the associated carbon atom in the ring.

When both $Z_5$ and $Z_6$ are carbonyl oxygens, then the first monomers are dioxanediones, or nitrogen-containing analogues thereof. When both $Z_7$ and $Z_8$ are carbonyl oxygens, then the second monomers are dioxanediones, or nitrogen-containing analogues thereof. R' is preferably hydrogen or hydrocarbyl.

In one embodiment, first monomers are dioxanediones, or nitrogen-containing analogues thereof, of the formula

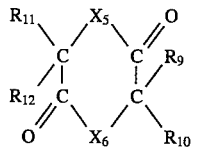

where,
independently for each such first monomer:
$X_5$ and $X_6$ are independently O or NR' and R' is independently H or hydrocarbyl; $R_9$ and $R_{10}$ combined have at most one carbon atom; and $R_{11}$ and $R_{12}$ combined have at most one carbon atom.

In one embodiment, second monomers comprise dioxanediones, or nitrogen-containing analogues thereof, of the formula

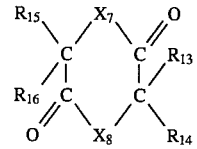

where,
independently for each such second monomer:
$X_7$ and $X_8$ are independently O or NR' and R' is independently H or hydrocarbyl; and $R_{13}$, $R_{14}$, $R_{15}$ and $R_{16}$ combined have at least four carbon atoms.

Preferably, at least one of $X_5$ and $X_6$ and at least one of $X_7$ and $X_8$ is oxygen. $R_9$, $R_{10}$, $R_{11}$, $R_{12}$, $R_{13}$, $R_{14}$, $R_{15}$ and $R_{16}$ can be the same or different from each other and can be any organic constituent such as hydrogen, hydrocarbyl, substituted hydrocarbyl, saturated hydrocarbyl, and others, including hetero-atom containing constituents. Preferably, $R_9$, $R_{10}$, $R_{11}$ and $R_{12}$ are hydrogen or hydrocarbyl, and if hydrocarbyl are more preferably saturated hydrocarbyl. $R_{13}$, $R_{14}$, $R_{15}$ or $R_{16}$ could be, for example, a furfural-based constituent, a vinyl-based constituent, a constituent having an aromatic ring. $R_{13}$ and $R_{14}$ or $R_{15}$ and $R_{16}$, respectively, could connect to form a single constituent, such as a cyclic constituent in which the ring of the constituent includes a carbon atom of the dioxane ring, such as in a spiro compound, such as, for example:

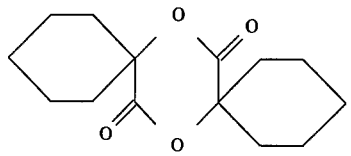

Preferably, however, $R_{13}$, $R_{14}$, $R_{15}$ and $R_{16}$ are hydrogen or hydrocarbyl, and if hydrocarbyl are more preferably saturated hydrocarbyl.

In one embodiment, first monomers have a molecular weight less than about 145. Such first monomers could be, for example, lactide, and/or glycolide.

In one embodiment, second monomers comprise tetramethyl glycolide. In another embodiment, second monomers comprise the cyclic diester of α-hydroxyisovaleric acid. In another embodiment, second monomers comprise the cyclic diesters of α-hydroxycaproic acid. In another embodiment, second monomers comprise the cyclic diester of α-hydroxyisocaproic acid. In another embodiment, second monomers comprise the cyclic diester of α-hydroxyoctanoic acid.

In one embodiment, at least one of $R_{13}$ and $R_{14}$ and at least one of $R_{15}$ and $R_{16}$ are hydrocarbyl radicals having from two to three carbon atoms. In another embodiment, at least one of $R_{13}$, $R_{14}$, $R_{15}$ and $R_{16}$ is a radical having from 4 carbon atoms to about 24 carbon atoms, preferably from about 4 carbon atoms to about 16 carbon atoms, and more preferably from about 4 carbon atoms to about 10 carbon atoms. In one preferred embodiment, the total number of carbon atoms in $R_{13}$, $R_{14}$, $R_{15}$ and $R_{16}$ combined is at least 5 and more preferably from 5 to about 12. In one embodiment, at least one of $R_{13}$ and $R_{14}$ and at least one of $R_{15}$ and $R_{16}$ are saturated hydrocarbyl radicals.

In one embodiment, one of $R_{13}$ and $R_{14}$ is isopropyl and the other is hydrogen, and one of $R_{15}$ and $R_{16}$ is isopropyl and the other is hydrogen. In another embodiment, one of $R_{13}$ and $R_{14}$ is propyl and the other is methyl, and one of $R_{15}$ and $R_{16}$ is propyl and the other is methyl.

In one embodiment, the constituents $R_{13}$ and $R_{14}$ are the same as the constituents $R_{15}$ and $R_{16}$, such as would be the case, for example, for a symmetrically substituted dioxanedione. In another embodiment, the total number of carbon atoms in $R_{13}$ and $R_{14}$ combined is different than the number of carbon atoms in $R_{15}$ and $R_{16}$ combined, such as would be the case, for example, for an unsymmetrically substituted dioxanedione.

In one embodiment, first monomers comprise from about 50 weight percent to about 99 weight percent of the total monomers from which the polymer is prepared, such as, for example, in a monomer mixture comprising both first monomers and second monomers. Preferably, first monomers comprise from about 80 weight percent to about 99 weight percent of the total monomers, more preferably from about 90 weight percent to about 99 weight percent of the total monomers, and most preferably from about 90 weight percent to about 97 weight percent of total monomers.

In one embodiment, second monomers comprise from about 1 weight percent to about 50 weight percent of the total monomers from which the polymer is prepared. Preferably, second monomers comprise from about 1 weight percent to about 20 weight percent of the total monomers, more preferably from about 1 weight percent to about 10 weight percent of the total monomers, and most preferably from about 3 weight percent to about 10 weight percent.

Preparation of Monomers

Cyclic compounds that may be used as monomers for manufacturing the polymers of the present materials can be prepared using any suitable method. Dioxanedione monomers, or nitrogen-containing analogues thereof, are preferably prepared directly from noncyclic α-hydroxycarboxylic acid esters or nitrogen-containing analogues, such as α-hydroxyamides, or from derivatives, such as salts, of either, thereby avoiding problems inherent with conventional backbiting methods. Such esters, amides and derivatives thereof can be prepared from base molecules, such as for example, α-hydroxycarboxylic acids and/or α-hydroxyamides. A more detailed discussion of methods useful for producing cyclic compounds, such as dioxaneones, and particularly dioxanediones, or nitrogen-containing analogues thereof, directly from noncyclic esters, or nitrogen-containing analogues such as amides, is provided in co-pending, commonly assigned U.S. application Ser. No. 07/854,559 for "Method to Produce Cyclic Esters", by Benecke et al., filed Mar. 19, 1992, and U.S. application Ser. No. 08/128,797 for "Method to Produce Cyclic Esters", by Verser et al., filed on even date herewith, both of which are incorporated herein in their entireties.

To better describe the production of cyclic compounds such as dioxanediones, or nitrogen-containing analogues thereof, directly from the noncyclic ester species, the following nomenclature, as more fully explained in U.S. application Ser. No. 07/854,559, may be used. Base molecules, such as α-hydroxycarboxylic acids, α-hydroxyamides, and salts and other derivative compounds (e.g., esters, ethers and salts with other than base molecules) of the foregoing are referred to as $Y_1A$. $Y_2A$ refers to a noncyclic, linear dimer, such as, for example, a molecule formed by a single reaction between any two $Y_1A$ molecules to form a noncyclic, straight chain, dimer having an ester or amide linkage. For example, the molecule formed by a single esterification of two α-hydroxycarboxylic acid base molecules would be a $Y_2A$. A $Y_3A$ refers to a noncyclic, linear trimer of base molecules having ester and/or amide linkages. $Y_4A$ refers to a noncyclic, linear tetramer having ester and/or amide linkages and $Y_nA$ refers to a noncyclic, linear n-mer. It should be recognized that $Y_2A$ is not limited by its method of formation, and could, for example, be formed by depolymerization, or by another decomposition reaction, of a larger oligomeric molecule, such as from a $Y_3A$ or a $Y_4A$ or a larger $Y_nA$. Likewise, any $Y_nA$ could be a depolymerization product of a larger oligomer. As used herein, YA without subscript generally denotes at least one of and generally a mixture of two or more of $Y_1A$, $Y_2A$, $Y_3A$, and $Y_4A$, or a solution thereof. When Y is substituted by L or G, specific corresponding compounds based on lactic acid and glycolic acid, respectively, are meant. For example, LA refers to $L_1A$, $L_2A$, $L_3A$, $L_4A$, etc. YD refers generically to a dioxanedione, or a nitrogen-containing analog thereof. LD refers specifically to lactide. As used herein, an amide refers to molecules that have an acyl group, being the nitrogen-containing analogue of a carboxyl group such as would be the case for a nitrogen-containing analogue of a carboxylic acid, and also molecules that have an amide linkage, such as would be the case for a nitrogen-containing analogue of an ester linkage.

A cyclic compound of dioxanedione, or a nitrogen-containing analogue thereof, derived from $Y_1A$ is produced by providing a compound mixture containing components including but not limited to YA, and treating the feedstream to form cyclic compounds which may be used as monomers for polymers of the present materials, as previously described. Not to be bound by theory, it is believed that the cyclic ester, or nitrogen-containing analogue, is formed primarily directly from a linear dimer, i.e., from $Y_2A$. Under certain reaction conditions, however, it is believed that $Y_3A$ and $Y_4A$ also contribute to dioxanedione formation. As used herein, forming the dioxanedione primarily directly from $Y_2A$ refers to a reaction in which $Y_2A$, such as $Y_2A$ already present in the feedstream or $Y_2A$ formed by an esterification reaction between two $Y_1A$ molecules, is converted to a cyclic compound of dioxanedione or a nitrogen-containing analogue thereof by ring-closing esterification or by a ring-closing formation of an internal amide linkage. That is, the cyclic compound is not formed by backbiting of polyester chains, as described in the prior art when a dioxanedione is formed from $Y_5A$ or greater.

In one embodiment, cyclic esters or nitrogen-containing analogues thereof such as amides, including dioxanediones, are prepared from a noncyclic ester or nitrogen-containing analogue thereof, by treatment including removal of water from a compound mixture including reactive components and an organic or silicon-based solvent.

In this embodiment, water initially in the compound mixture is removed rapidly leading to an essentially dehydrated feedstream having a water concentration of less than about 2 wt %. Water formed by the esterification reactions is preferably removed essentially as it is formed. In particular, water is typically removed at a rate such that the concentration of water in the treated compound mixture is less than about 2 wt %, more preferably less than about 1 wt %, and even more preferably less than about 0.5 wt %.

Water can be removed from a compound mixture by a variety of methods, including, but not limited to: evaporation; a solvent-based reaction process, such as a reactive distillation process; removal of water as an azeotrope from a feedstream in which the reactive components are diluted in a solvent which forms an azeotrope with water; adding a water-getter which preferentially reacts with water; using molecular sieves or partitioning (e.g., osmotic) membranes;

using anhydrous salts that form hydrated crystals with water; contacting the feedstream with water absorptive materials, such as polysaccharides or silica.

As noted above, the reaction is preferably conducted in a solvent. Preferably, the reactive components of the compound mixture are present in dilute concentration in a solvent. For example, the concentration of YA can be less than about 25% by weight of a feedstream. Preferably, YA species are 100% soluble in the solvent at reaction conditions.

Preferably, the solvent is relatively polar because it is believed that more polar solvents, such as anisole, favor the selective formation of YD over $Y_5A$ and higher oligomers. Suitable solvents for use in the present invention can include aromatic solvents, aliphatic solvents, ethers, ketones, silicon-based solvents and halogenated solvents. Preferred solvents are aromatic solvents.

Specific solvents of the present invention include 2-butanone, 2-heptanone, 2-hexanoe, 2-pentanone, acetone, anisole, butyl ether, ethyl ether, isopropyl ether, methyl-phenyl ether, benzene, cumene, m-xylene, o-xylene, p-xylene, toluene, cyclohexane, heptane, hexane, nonane, octane, 1-pentene, 2-octanone, dimethyl sulfoxide, phenetole, 4-methyl anisole, 1,3-dimethoxybenzene, 1,2-dimethoxybenzene, 1,4-dimethoxybenzene, mesitylene, chlorobenzene, 1,2-dichlorobenzene, 1,3-dichlorobenzene, 1,4-dichlorobenzene, 2-chlorotoluene, 4-chlorotoluene, veratrole, and 3-chlorotoluene. Preferred solvents include toluene, xylene, anisole, phenetole, 4-methyl anisole, 1,3-dimethoxy benzene, and mesitylene. Particularly preferred solvents of the present invention include xylene, anisole and 4-methyl anisole.

Substituted aromatic solvents are particularly preferred for the present invention. Such solvents are typically polar and thus, provide high selectivity. Also preferred are di-substituted aromatics, such as 4-methyl anisole.

The cyclic compound formed by the above-described process can be recovered and purified, for example, by crystallization, solvent extraction, distillation, membrane partitioning, washing with solvent, chromatography, sublimation, and combinations thereof. Preferably, the cyclic compound is a dioxanedione, or a nitrogen-containing analogue thereof, all as previously described.

The role played by water in the present process can be appreciated by reference to the following equilibrium reactions:

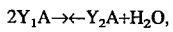

$2Y_1A \rightleftharpoons Y_2A+H_2O$,

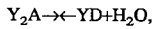

$Y_2A \rightleftharpoons YD+H_2O$,

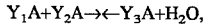

$Y_1A+Y_2A \rightleftharpoons Y_3A+H_2O$, etc.

Thus, it will be observed that $Y_1A$ is in equilibrium with higher oligomers of $Y_1A$, cyclic esters and water. By removing water, the reactions are driven to the right and, conversely, by adding water the reactions are driven to the left.

Different monomers useful in preparing polymers for the present materials, as previously discussed, can be prepared individually and mixed together for polymerization, or they can be prepared together. When prepared individually, for example, a first monomer could be prepared from first YA species (e.g., from a first $Y_2A$). A second, different monomer could be separately prepared from second YA species (e.g., from a second $Y_2A$). The first and second monomers, preferably following purification of each, could then be mixed together and copolymerized to form a polydioxaneone useful in making the materials of the present invention.

In another embodiment, a first monomer and a second monomer could both be prepared from a single feed. The feed could contain, for example, two different base molecule species, preferably with one present in a much lower concentration than the other. In such a feed mixture, the $Y_2A$ would comprise first linear dimers representative of two first base molecules and would also comprise second two linear dimers representative of one of a first base molecule and one of a second base molecule. If the concentration of first base molecules is sufficiently high compared to second base molecules, then the feed would not comprise appreciable amounts of $Y_2A$ other than the two already described. The monomers produced would then comprise primarily first monomers that are symmetrically substituted dioxanediones, or nitrogen-containing analogues thereof, being the cyclic compounds representative of two of the first base molecule. The monomers produced would also comprise a smaller amount of second monomers that are unsymmetrically substituted dioxanediones, or nitrogen-containing analogues thereof, being the cyclic compounds representative of one of a first base molecule and one of a second base molecule. For example, lactic acid (i.e., α-hydroxypropanoic acid) and α-hydroxyoctanoic acid could be mixed as first and second base molecules in a feed. First monomers would then be a cyclic diester representative of two lactic acids (i.e., lactide) and second monomers would then be a cyclic diester representative of one lactic acid and one α-hydroxyoctanoic acid. This process could also be used to make more than two different dioxanedione monomers together.

Preparation of Polymers

The polymer of the present materials can be prepared by a variety of polymerization techniques. Dry conditions should be maintained throughout. Preferably, the polymerization reaction is conducted in the liquid phase in a closed, evacuated vessel. Alternatively, the polymer can be prepared at atmospheric pressure with the polymerization mixture blanketed by an inert gas such as, for example, nitrogen. If the polymerization reaction is conducted in the presence of water or oxygen, such as would be the case for air, some undesirable discoloration, chain termination or catalyst deactivation can occur with a resulting decrease in molecular weight and tensile strength of the final polymer.

First monomers may be melted and mixed in a melt with second monomers. Typically, the polymerization is conducted in a melt above the melting point of the monomers and below a temperature at which degradation of monomers or of the resulting polymer occurs. The polymerization temperature will typically be below about 200° C. Catalyst is preferably used to enhance the polymerization Catalyst particles may be added directly to the melted monomers. The catalysts used in the polymerization reaction of the present invention may be metal salts and esters of carboxylic acids containing up to 18 carbon atoms. Examples of such acids are formic, acetic, propionic, lactic, butyric, valetic, caproic, 2-ethylhexanoic, caprylic, pelargonic, capric, lauric, myristic, palmitic, stearic, and benzylic acids. Several other catalysts may also be used. These include cationic catalysts including hydrogen chloride, hydrogen iodide, hydrogen bromide, boron triflouride, triflourosulfonic acid, and Nafion™ (an acidic catalyst available from du Pont). Anionic catalysts may also be used. These include derivatives of alkali metals including alkoxides and organometallic compounds. Alkali metal alkoxides include, for example, sodium methoxide, potassium t-butoxide, lithium t-butoxide, etc. Organometallic compounds include, for example, butyl lithium. Amines, including triethyl amine and DABCO™ (an amine-based catalyst available from Texaco) may also be used. Derivatives of divalent and trivalent metals may also be used. Included are oxides, carbonates and halides, such as those of zinc and magnesium, and carboxylates such as zinc tartrate, cadmium tartrate, and tin octoate. Also included are hydrolysis, alcoholysis, and aminolysis products of organometallic compounds such as organometallic compounds of zinc, cadmium, magnesium, and aluminum treated with water or ammonia. Certain binary or ternary systems may also be used as catalysts, including a binary system of an aluminum alcoholate with zinc chloride, a binary system of triphenyltin bromide with triphenylphosphorus, and a tertiary system of an aluminum trialkyl with water and acetylactone. Additional catalysts, often useful for homogeneous polymerization, include aluminum porphyrins, a zinc-containing complex of the formula $[(CH_3OCH_2CH(CH_3)O)_2Z_n]_2 \cdot [C_2H_6Z_nOCH(CH_3)CH_2OCH_3]_2$, and an aluminum alkoxide derivative of the formula $(RO)_2AlOZ_nOAl(OR)_2$, with R preferably being an alkyl.

Although a wide range of catalysts are possible, as discussed, preferred catalysts are alkoxides, and more preferred are alkoxides of alkali metals, such as lithium t-butoxide. The best catalyst for a particular situation, however, depends upon the specific monomers and specific polymerizing conditions used. In some instances, it may be desirable to use co-catalysts, such as to enhance production of higher molecular weight polymers and to inhibit production of lower molecular weight oligomers.

The catalyst is used in normal catalytic amounts for polymerization. For example, a stannous 2-ethylhexanoate catalyst concentration in a range of about 0.001 to about 2 percent by weight, based on total weight of the monomers or comonomers, is suitable for polymerization of lactide. A catalyst concentration in the range of about 0.01 to about 1.0 percent by weight is generally preferred. Particularly preferred is a catalyst concentration in the range of about 0.02 to about 0.5 percent by weight. The exact amount of catalyst in any particular case depends to a large extent upon the catalyst employed and the operating variables, including time, temperature, the desired rate of reaction, and the desired molecular weight of the polymer.

The reaction time of the polymerization process is dependent on various reaction variables, including reaction temperature, polymerization catalyst, amount of catalyst, degree of mixing, and whether a solvent is used. The reaction time can vary from a matter of minutes to a period of hours or days, depending upon the particular set of conditions which is employed. Heating of the mixtures of monomers or comonomers is continued until the desired level of polymerization is attained. For example, the extent of polymerization can be determined by analysis for residual monomers. In general, it is preferred to conduct the polymerization in the absence of impurities which contain active hydrogen since the presence of such impurities tends to deactivate the catalyst and/or increase the reaction time. It is also preferred to conduct the polymerization under substantially anhydrous conditions.

The polymer of the present invention can be prepared by bulk polymerization, suspension polymerization or solution polymerization. The polymerization can be carried out in the presence of an inert normally-liquid organic vehicle such as, for example, aromatic hydrocarbons such as benzene, toluene, xylene, ethylbenzene and the like; oxygenated organic compounds such as anisole, dimethyl and diethyl ethers of ethylene glycol; normally-liquid saturated hydrocarbons including open cha, cyclic and alkyl-substituted cyclic saturated hydrocarbons such as hexane, heptane, cyclohexane, decahydronaphthalene; and the like.

The polymerization process can be conducted in a batch, semi-continuous, or continuous manner. In preparing the monomeric reactants and catalysts for subsequent polymerization, they can be admixed in any order according to known polymerization techniques. Thus, the catalyst can be added to one comonomeric reactant. Thereafter, the catalyst-containing comonomer can be admixed with another comonomer. In the alternative, comonomeric reactants can be admixed with each other. The catalyst can then be added to the reactant mixture. If desired, the catalyst can be dissolved or suspended in an inert, normally-liquid organic vehicle. If desired, the monomeric reactants either as a solution or a suspension in an inert organic vehicle can be added to the catalyst, catalyst solution or catalyst suspension. Alternatively, the catalyst and comonomeric reactants can be added to a reaction vessel simultaneously. The reaction vessel can be equipped with a conventional heat exchanger and/or mixing device. The reaction vessel can be any equipment normally employed in the art of making polymers. One suitable vessel, for example, is a stainless steel vessel.

EXAMPLES

Example 1

This example demonstrates preparation of the cyclic diester of α-hydroxyisobutyric acid.

A 200 ml sample of an organic solvent is provided that is composed of 10% by weight anisole and 90% by weight xylene. In the organic solvent is dissolved commercially available α-hydroxyisobutyric acid feed. The resulting mixture has approximately 5% by weight α-hydroxyisobutyric acid feed with the remainder being solvent. From about 0.2% to about 2.0% by weight of sulfuric acid, relative to the α-hydroxyisobutyric acid, is added to the mixture. The mixture is heated to a boil and vapor is refluxed while water from the vapor is collected in a dean-stark tube. A sample taken from the mixture after several hours of such refluxing is analyzed by high performance liquid chromatography (HPLC). HPLC with mass spectrometry detection shows the presence of the cyclic diester of α-hydroxyisobutyric acid in the sample.

Example 2

This example demonstrates preparation of the cyclic diester of α-hydroxyisovaleric acid.

A mixture having about 5% by weight of commercially available α-hydroxyisovaleric acid dissolved in 200 ml of xylene is prepared in the manner as described in Example 1. A small amount of sulfuric acid (from about 0.2% to about 2% by weight relative to α-hydroxyisovaleric acid) is added to the mixture. The mixture is heated to a boil and vapor is refluxed while water from the vapor is collected in a dean-stark tube as described in Example 1. A sample taken from the mixture after several hours of such reflux shows the presence of the cyclic diester of α-hydroxyisovaleric acid, using HPLC with mass spectrometry.

Examples 3–5

Cyclic diesters of -hydroxycaproic acid, α-hydroxyisocaproic acid and α-hydroxyoctanoic acid are prepared in xylene according to the procedure of Example 2. Commercially available α-hydroxycarboxylic acids are used as feed for each of the respective tests. Analyzing samples by HPLC with mass spectrometry shows that the cyclic diesters are prepared.

Example 6

This example demonstrates preparation and purification of the cyclic diester of α-hydroxyoctanoic acid. To a three-neck flask fitted with a heating mantel, pot thermometer, magnetic stirrer, dean-stark tube, reflux condenser and a rubber septum is added approximately 5 g of α-hydroxyoctanoic acid, 95 ml of toluene and 0.22 g of Dowex-50™ catalyst (available from Dow Chemical). The mixture was heated to reflux (approximately 116° C.), and aliquots were taken at various time intervals over 48 hours. Remaining α-hydroxyoctanoic acid and noncyclic oligomers in the aliquots were derivatized with diazomethane to facilitate gas chromatography analysis. Gas chromatography/mass spectrometry shows the presence of the cyclic diester of α-hydroxyoctanoic acid in samples taken at 1, 29 and 48 hours of reflux.

Cyclic diester remaining in the reaction mixture at the end of the experiment is isolated from the feed α-hydroxyoctanoic acid using an ion exchange resin (Amberlyst™ A-21 available from Rohm & Haas) from about 200 to about 300 ml of the ion exchange resin was placed in a 1 inch inner diameter chromatography column. A 1:1 toluene/acetone solution (by volume) is prepared and used to treat the ion exchange resin until effluent from the resin is neutral. A sample of the reaction mixture is then diluted 1:1 with acetone (by volume) and the diluted reaction mixture is passed over the resin and the eluate is recovered. Analysis of the eluate shows that it is predominantly composed of the cyclic diester of α-hydroxyoctanoic acid. Based on the amount of cyclic ester in the eluate, the yield of isolated cyclic ester is approximately 15%.

Example 7

This example demonstrates production of the cyclic ester of α-hydroxyoctanoic acid using a mesitylene (1,3,5-trimethylbenzene) solvent. Three experiments are performed using α-hydroxyoctanoic acid concentrations in mesitylene of 20%, 10%, and 5% (wt./vol.) respectively. Reaction mixtures are heated at reflux for 5.5 hours according to the procedure of Example 6. Aliquots are periodically taken throughout the course of each reaction and samples are derivatized and analyzed by gas chromatography. The 20% solution gives the highest yields of cyclic esters, peaking at between about 25 and 30% yield at 2.5 to 3.5 hours of reflux. Yields in the 10% solution peak at about 25% at about 3.5 hours of reflux. Yields in the 5% solution reach about 15% after 5.5 hours.

While various embodiments of the present invention have been described in detail, it is apparent that modifications and adaptations to those embodiments will occur to those skilled in the art. It is to be expressly understood, however, that such modification and adaptations are within the scope of the present invention, as set forth in the following claims.

What is claimed is:

1. A degradable foam material comprising a hydrolytically degradable polymer in a foam form, said polymer comprising:

(a) a backbone chain;

(b) first repeating units of the formula

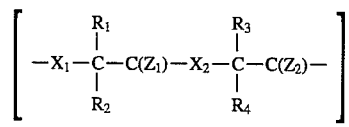

where, independently for each such first repeating unit:

X and $X_2$ are independently O or NR' and R' is independently H, hydrocarbyl, substituted hydrocarbyl or a hydrocarbyl derivative; $R_1$, $R_2$ and $Z_1$ combined have at most one carbon atom; $R_3$, $R_4$ and $Z_2$ combined have at most one carbon atom;

$Z_1$ and $Z_2$ are each independently one or more constituent group extending from the backbone chain and being covalently bonded to an associated carbon atom in the backbone chain, at least one of $Z_1$ and $Z_2$ being oxygen which forms a carbonyl group with the associated carbon atom in the backbone chain; and the molecular weight of such a first repeating unit is less than about 145; and (c) from about 1 weight percent to about 50 weight percent, based on the total weight of said polymer, of second repeating units of the formula

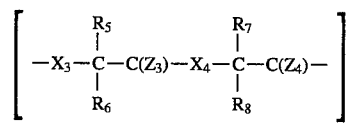

where, independently for each such second repeating unit:

$X_3$ and $X_4$ are independently O or NR' and R' is independently H, hydrocarbyl, substituted hydrocarbyl or a hydrocarbyl derivative; $R_5$, $R_6$, $R_7$ and $R_8$ combined have at least four carbon atoms; $Z_3$ and $Z_4$ are each independently one or more constituent group extending from the backbone chain and being covalently bonded to an associated carbon atom in the backbone chain, at least one of $Z_3$ and $Z_4$ being oxygen which forms a carbonyl group with the associated carbon atom in the backbone chain.

2. The foam material of claim 1, wherein said second repeating units are of the formula

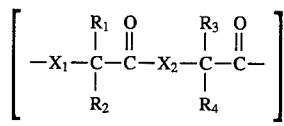

where, independently for each such second repeating unit:

$X_1$ and $X_2$ are independently O or NR' and R' is independently H, hydrocarbyl, substituted hydrocarbyl or a hydrocarbyl derivative; $R_1$ and $R_2$ combined have at most one carbon atom; $R_3$ and $R_4$ combined have at most one carbon atom; and the molecular weight of such a first repeating unit is less than about 145.

3. The foam material of claim 1, wherein said second repeating units are of the formula

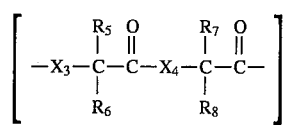

where, independently for each such second repeating unit:

$X_3$ and $X_4$ are independently O or NR' and R' is independently H, hydrocarbyl, substituted hydrocarbyl or a hydrocarbyl derivative; $R_5$, $R_6$, $R_7$ and $R_8$ combined have at least four carbon atoms.

4. The foam material of claim 1, wherein at least one of $X_1$, $X_2$, $X_3$ and $X_4$ is oxygen.

5. The foam material of claim 1, wherein $X_1$, $X_2$, $X_3$ and $X_4$ are oxygen.

6. The foam material of claim 1, wherein one of $R_1$ and $R_2$ is methyl and the other of $R_1$ and $R_2$ is H and wherein one of $R_3$ and $R_4$ is methyl and the other of $R_3$ and $R_4$ is H.

7. The foam material of claim 1, wherein $R_1$, $R_2$, $R_3$ and $R_4$ are all H.

8. The foam material of claim 1, wherein at least one of $R_5$, $R_6$, $R_7$ and $R_8$ is hexyl.

9. The foam material of claim 1, wherein $R_5$, $R_6$, $R_7$ and $R_8$ are all methyl.

10. The foam material of claim 1, wherein at least one of $R_5$ and $R_6$ is isopropyl and at least one of $R_7$ and $R_8$ is isopropyl.

11. The foam material of claim 1, wherein one of $R_5$ and $R_6$ is propyl and the other of $R_5$ and $R_6$ is methyl and wherein one of $R_6$ and $R_7$ is propyl and the other of $R_6$ and $R_7$ is methyl.

12. The foam material of claim 1, wherein second repeating units are of a formula that would result from ring opening polymerization of a cyclic diester of an α-hydroxyisovaleric acid or nitrogen-containing analogue thereof.

13. The foam material of claim 1, wherein second repeating units are of a formula that would result from ring-opening polymerization of a cyclic diester of an α-hydroxyisocaproic acid or nitrogen-containing analogue thereof.

14. The foam material of claim 1, wherein the total number of carbon atoms in $R_5$, $R_6$, $R_7$ and $R_8$ combined is at least 5.

15. The foam material of claim 1, wherein said polymer has a weight average molecular weight of greater than about 30,000.

* * * * *